US005789586A

United States Patent [19]
Robinson

[11] Patent Number: 5,789,586
[45] Date of Patent: Aug. 4, 1998

[54] EFFICIENT FUNCTIONALIZATION OF PORPHYRIN DERIVATIVES POSSESSING SULFONIC ACID GROUPS

[75] Inventor: Byron Robinson, Santa Barbara, Calif.

[73] Assignee: PDT Pharmaceuticals, Inc., Santa Barbara, Calif.

[21] Appl. No.: 889,114

[22] Filed: Jul. 7, 1997

Related U.S. Application Data

[63] Continuation of Ser. No. 492,954, Jun. 20, 1995, abandoned.
[51] Int. Cl.$^6$ ................................................. C07D 487/22
[52] U.S. Cl. .......................... 540/472; 540/145; 540/465; 540/474; 534/11; 534/12; 534/13; 534/15
[58] Field of Search ........................ 540/145, 472, 540/473, 474

[56] References Cited

U.S. PATENT DOCUMENTS

| | | | |
|---|---|---|---|
| 5,156,840 | 10/1992 | Goers et al. | 514/410 |
| 5,250,668 | 10/1993 | Morgan et al. | 540/145 |
| 5,281,616 | 1/1994 | Dixon et al. | 540/145 |
| 5,484,915 | 1/1996 | Gregory et al. | 540/136 |

Primary Examiner—Mukund J. Shah
Assistant Examiner—Pavanaram K. Sripada
Attorney, Agent, or Firm—Michael G. Petit

[57] ABSTRACT

A method for preparing functionalized derivatives of organic or inorganic compounds and tetrapyrrolic compounds in particular, all of which compounds have at least one sulfonic acid group, by first preparing a sulfonyl halide intermediate of the compound then reacting the intermediate with a second compound having a reactive hydroxyl or amine group to yield the desired sulfonylamide or sulfonic esters thereof. The method may be used to produce a variety of photosensitive compounds having different functionality. For example, sulfonamide or sulfonic ester reaction products of the tetrapyrrolic compounds or other photosensitive organic molecules may exhibit an enhanced ability to localize at a particular target site for phototherapy. The method provides means for altering the functionality of sulfonic acid-containing photosensitive compounds to produce derivatives thereof which may aid in the detection and/or phototherapy of diseased sites or provide functionality having enhanced affinity and exhibiting improved binding to site specific receptors within a diseased target tissue such that the therapy is improved.

7 Claims, 2 Drawing Sheets

EFFICIENT FUNCTIONALIZATION OF PORPHYRIN DERIVATIVES POSSESSING SULFONIC ACID GROUPS

CROSS-REFERENCE TO RELATED APPLICATIONS

This is a continuation of application Ser. No. 08/492,954, filed Jun. 20, 1995, now abandoned.

BACKGROUND OF THE INVENTION

1. Field of the Invention

This invention is a method for preparing functional derivatives of compounds containing a sulfonic acid group and more particularly to a method for making photosensitive compounds useful for phototherapy and even more particularly to a method for making functional derivatives of porphyrin compounds and similar photosensitive compounds which possess at least one sulfonic acid group.

2. Prior Art

Porphyrins and related tetrapyrrolic macrocycles as well as many other light absorbing compounds have application in photosensitized medicine, especially in the field of photodynamic therapy (PDT). Photosensitive compounds useful for PDT have a selective affinity for diseased tissue and accumulate in such tissue to a greater extent (i.e. have a higher concentration) than in normal tissue. Thus, there is differential uptake of photosensitive compounds between normal and abnormal tissue as the compound not only accumulates to a greater extent in disease tissue, but persists longer as well. Phototherapy involves the localization of a photosensitizing agent in or near a diseased target tissue within the body. The photosensitive compound (photosensitizer), upon illumination and in the presence of oxygen, produces cytotoxic species of oxygen such as singlet oxygen or oxygen radicals, which destroy the diseased target tissue. The photosensitizer is innocuous at the therapeutic dose, and only becomes active on illumination with light of a specific wavelength dictated by the absorption properties of the photosensitizer. PDT offers a level of control or selectivity in the treatment of diseases not currently found with current systemic methods such as chemotherapy. Photodynamic therapy has wide application to modern medicine, targeting diseased tissue such as cancers, cardiovascular lesions such as restenosis and plaques, psoriasis, viral infections, benign prostate hyperplasia and diabetic retinopathy. In addition, photodynamic therapy may also be useful for the sterilization of blood, an area of increasing concern, especially now with the advent of AIDS and the transmission of HIV through blood transfusions.

Most research on PDT has centered around a porphyrin mixture marketed as Photofrin II®. Photofrin II® has recently been recommended for approval for the treatment of obstructed endobronchial tumors by the Food and Drug Administration Advisory Panel. Although the use of Photofrin II® as a photosensitizer has demonstrated the potential benefits of PDT, it has a number of disadvantages. One disadvantage is that Photofrin II® is a complex mixture consisting of ill-defined porphyrin dimers, trimers and oligomers. Each of these components has varied subcellular localizations depending on structure and inherent differences in photophysical properties. This makes the interpretation of pharmacokinetic data difficult. In addition, the composition of the oligomers is often difficult to reproduce and may change depending on the storage conditions in solution. Hence, the true "active components" may vary considerably. A second disadvantage is that Photofrin II® has a less than optimal light absorption profile (630 nm, $\epsilon$~3,000). It is well known that longer wavelength light penetrates deeper into tissues. While not all applications of PDT require deep penetration of light, many, if not most applications require the maximum depth of light penetration possible (for example the treatment of brain tumors). A third disadvantage is that Photofrin II® has a severe adverse normal skin response to light, which often lasts for up to 12 weeks after therapy. During this time patients must avoid strong light, otherwise severe burns and edema occur.

Several well characterized second generation sensitizers such as tin etiopurpurin (SnET2), zinc phthalocyanine (ZnPc), benzoporphyrin derivative (BPDMA), and meta-tetrahydroxyphenyl chlorin (THPC) have been described (see, for example, U.S. Pat. No. 5,051,415 to Morgan et al.) and are currently in phase I/II clinical trials. The continued development of new photosensitizers exhibiting improved therapeutic efficacy is crucial to the future progress of the therapy.

Several reactive groups are widely used in organic chemistry to change the functionality of tetrapyrrolic compounds. Those most commonly used are the carboxylic acid group, the alcohol group, the amine group, and the ether group. A group which has received little attention in tetrapyrrolic chemistry with respect to chemical modification is the sulfonic acid group. The sulfonic acid group may be modified to form a sulfonyl halide group which, under certain conditions, can be linked directly to amine or alcohol containing compounds. As shown in scheme 1 below (wherein P—SO$_3$H is a compound having a sulfonic acid group thereon).

Scheme 1

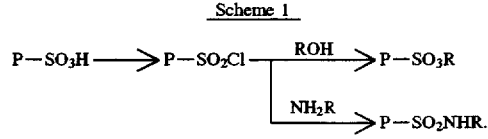

In general the sulfonic acid group is reacted with thionyl chloride or phosphorus pentachloride to give the sulfonyl chloride derivative. This type of transformation is well established in organic chemistry. In porphyrin chemistry however, a number of problems arise when reagents such as thionyl chloride or phosphorus pentachloride are used for the preparation of porphyrin sulfonylchlorides. Under the reaction conditions necessary to prepare the sulfonyl chloride derivatives, generally warming or refluxing (phosphorus pentachloride and thionyl chloride respectively), halogenation of the meso-positions occurs. An example of this is shown below in scheme 2.

Scheme 2

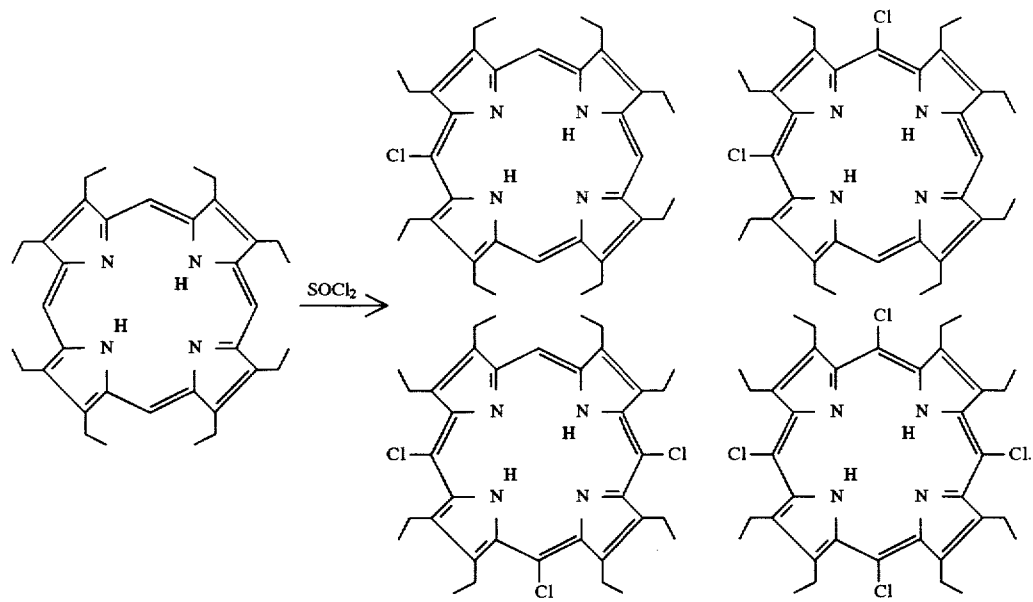

Thus, if octaethylporphyrin is refluxed in thionyl chloride, a mixture of mono-, di-, tri, and tetra-chlorinated octaethylporphyrin is obtained. The yield of each is totally dependent on the reflux time and good yields of meso-tetrachlorinated octaethylporphyrin is obtained for longer reaction times. A similar reaction has been observed for the meso-chlorination of octaethylporphyrin when sulfuryl chloride is used, however the reaction is rapid and generally only the meso-tetrachlorinated octaethylporphyrin derivative can be isolated.

Phosporus pentachloride is a highly acidic chlorinating agent and in some cases the porphyrin macrocycle is destroyed under the conditions necessary to form the sulfonyl chloride moiety. As a consequence, an efficient route to the functionalization of tetrapyrrolic compounds by way of a sulfonic acid moiety has not been described.

As it is possible to generate a large number of compounds with different functionality via the chemistry outline in scheme 1, it is desirable to provide a method for functionalizing tetrapyrrolic compounds having desirable photodynamic properties via the a sulfonic acid linkage. The present invention provides a convenient means for preparing functionalized derivatives of tetrapyrrolic compounds utilizing compounds possessing a sulfonic acid moiety.

SUMMARY OF THE INVENTION

It is an object of the present invention to provide a method for making photosensitive pyrrolic compounds having properties useful in phototherapy in general and are useful in photodynamic therapy in particular.

It is a further object of the inventor to provide novel compounds having enhanced selective affinity for a particular tissue.

It is another object of the present invention to provide a photosensitive compound comprising a reaction product of: (A) P—$SO_3H$, where P is a pyrrolic derivative; and (B) $POCl_3$, $SOCl_2$ or $[(R)_2N=CHCl]^+X^-$ (where $X^-$ is a charge balancing ion), to provide the reaction product (C) P—$SO_2Cl$.

It is still another object of the present invention to provide a photosensitive compound comprising a reaction product of: (C) P—$SO_2Cl$, where P is a pyrrolic derivative; and (D)) alcohols or amine containing compounds.

It is a further object of the present invention to provide a reaction product of: (A) P—$SO_3H$, where P is either an organic compound or an inorganic compound; and (B) $POCl_3$ or $[(R)_2N=CHCl]^+X^-$, where $X^-$ is a charge balancing ion, to provide the reaction product (C) P—$SO_2Cl$.

It is still a further object of the present invention to provide a reaction product of: (A) P—$SO_3H$, where P is either an organic compound or an inorganic compound; and (B) $SOCl_2$, to provide the reaction product (C) P—$SO_2Cl$.

It is an object of the present invention to provide a reaction product of: (C) P—$SO_2Cl$, where P is either an organic compound or an inorganic compound; and (D) alcohols or amine containing compounds.

It is a particular object of the present invention to provide a method for modifying pyrrolic derivatives possessing one or more sulfonic acid group, such that a sulfonylhalide group is formed that may, in turn, be reacted with alcohols and amines to produce photosensitive compounds that may be used to diagnose and/or treat diseases such as atherosclerosis, restenosis, cancer, cancer pre-cursors, non-cancerous hyperprofiferating diseases, psoriasis, macular degeneration, glaucoma and viruses.

DESCRIPTION OF THE PREFERRED EMBODIMENTS

Figure 1:
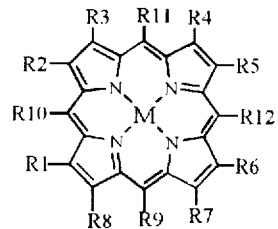

The present invention outlines an efficient method for derivatizing either photoactivatable or non photoactivatable compounds which compounds possess at least one sulfonic acid group. The compound bearing the sulfonic acid group is first converted to a sulfonylhalide moiety which may then be reacted with alcohols or amides such that sulfonyl ester or a sulfonyl amide linkage is produced. Additionally the sulfonyl halide group may then be further modified to form thiols or other functionalities derived from the original sulfonylhalide compound. Examples of the chemistry is outlined below.

Formation of P—SO$_2$Cl using POCl$_3$ or Vilsmeier reagents

As shown in Scheme 3 below, the reaction of octaethylbenzochlorin sulfonic acid (OEBCS) (1) (number in parenthesis refer to the compound indicated in the Scheme) with refluxing POCl$_3$ results in the synthesis of the corresponding sulfonyl chloride derivative (2). No evidence of mesochlorination is observed under these conditions. The sulfonylchloride derivative (2) is stable and may be stored for long periods of time at room temperature. Compound (2) may be reacted with either alcohols or amines to give sulfonate esters or sulfonylamides as shown in scheme 3. The reaction of the sulfonylchloride derivative (2) with sodium alkoxides produces almost quantitative yields of the sulfonate esters. Addition of alcohols in the presence of bases such as triethylamine or pyridine to (2) also gives the sulfonate esters. The sulfonylchloride group of (2) reacts very slowly with alcohols alone.

reagents, provides a very efficient route to the synthesis of sulfonylhalide functionalized benzochlorins. Of perhaps more importance is the type of functional group that may be added to the sulfonylhalide functionality of the benzochlorin nucleus. For example, amines, alcohols, amine alcohols, antibodies, amino acids, amine-containing sugars and nucleic acids may all be attached to this group providing they possess free amine or alcohol groups.

Functionalized benzochlorin iminium salts may be produced using similar chemistry as shown in Scheme 4 below. In this case, the production of iminium salts proceeds from the copper derivative of OEBCS, (3) via the use of Vilsmeier reagents. In addition to forming the sulfonylchloride moiety from the sulfonic acid, the Vilsmeier reagent also introduces the iminium functionality at the meso-position adjacent to the reduced pyrrole ring (4). The introduction of the iminium moiety at the meso-position is slow when the metallo-

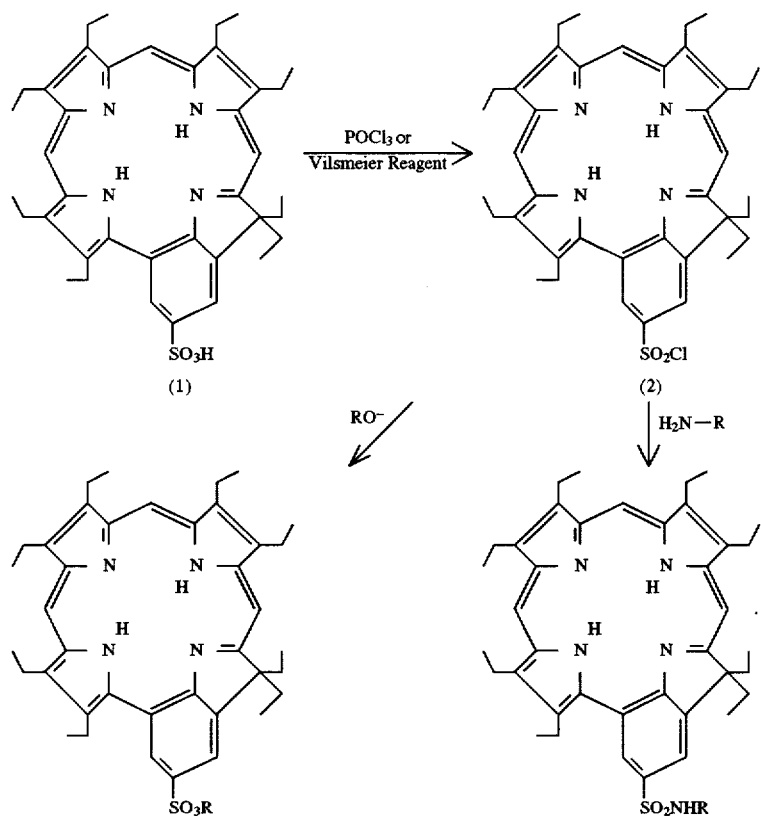

Scheme 3

The reaction of the sulfonylchloride derivative (2) with amines on the other hand, is rapid and quantitative. The difference in reactivity between alcohols and amines permits the synthesis of compounds from alcohol-containing amines (i.e.: H$_2$N(CH$_2$)$_3$OH) such that only the amine functionality reacts to give sulfonylamides. This selectivity permits the further linkage of other compounds to the free alcohol moiety.

Alternatively, the reaction of OEBCS (1) with Vilsmeier reagent, (for example, [(CH$_3$)$_2$N=CHCl]$^+$Cl$^-$), at room temperature in methylene chloride also produces the sulfonylchloride derivative (2) rapidly and in almost quantitative yield. As with POCl$_3$, no meso-chlorination is observed and (2) is easily isolated. Thus the synthesis of the sulfonyl chloride derivative (2) via the use Of POCl$_3$ or Vilsmeier benzochlorin possesses a sulfonic acid group and the metallo-benzochlorin sulfonylchloride derivatives may be isolated if desired, in good yield. The sulfonylchloride group, as before, reacts with amines to give the functionalized metallo-benzochlorin iminium salts. The choice of Vilsmeier regent also effects the functionality on the iminium group. For example, if the Vilsmeier regent is prepared from N,N-diethylfonnamide and POCl$_3$, the iminium moiety will possess ethyl groups attached to the nitrogen. Hence a range of functional group changes can be performed that include both the sulfonic acid moiety and the iminium functionality depending on the functionality on the Vilsmeier reagent.

Scheme 4

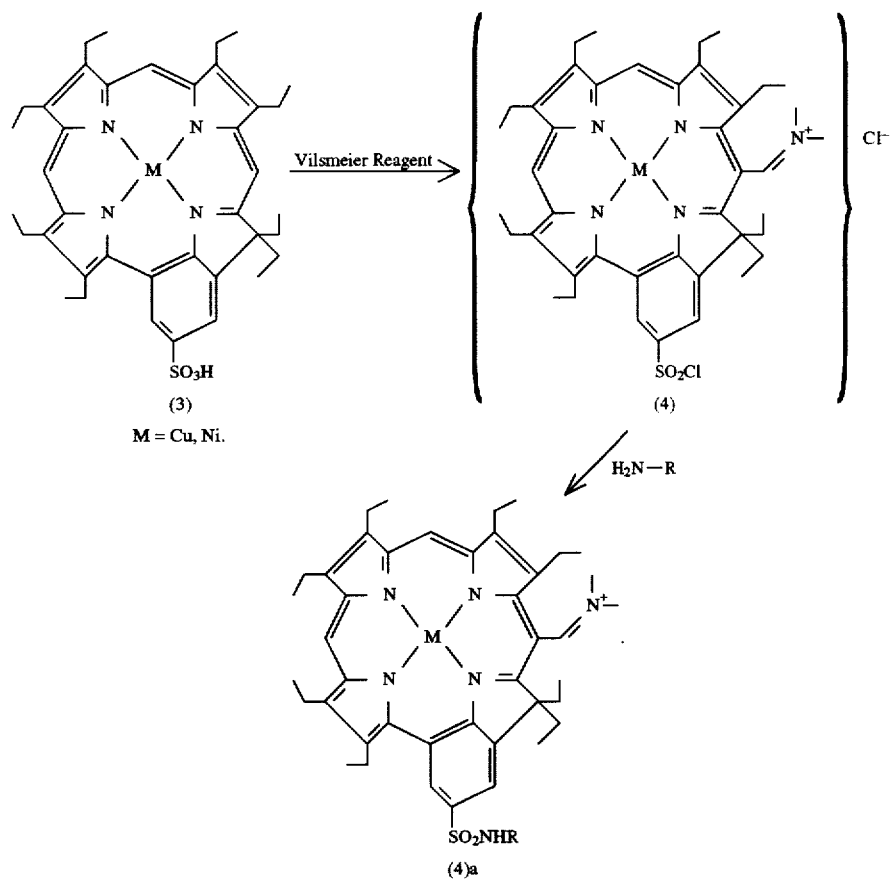

Formation of P-SO$_2$Cl using thionyl chloride (SOCl$_2$)

When thionyl chloride (SOCl$_2$) is used in place Of POCl$_3$ or Vilsmeier reagent to form the sulfonylchloride derivative (2), meso-chlorination as well as formation of the sulfonylchloride moiety occurs. Thus, with reference now to Scheme 5 below, heating OEBCS (1) in SOCl$_2$ gives 5,15 dichlorinated OEBC sulfonyl chloride derivative (5). The same meso-halogenation also occurs with octaethyl benzochlorin.

Scheme 5

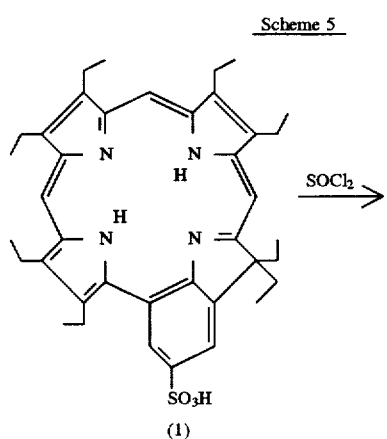

-continued
Scheme 5

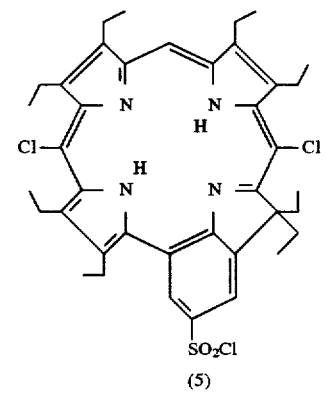

Compound (5) may also be reacted with alcohols or amines via similar chemistry as shown in scheme 1, to produce the corresponding amine or alcohol-linked compounds. It may be possible to functionalize the 5,15 mesopositions further by reacting the chlorines at these positions with suitable reagents. Hence the chemistry outlined above can be used to produce a wide range of functionalized benzochlorin compounds.

Moreover, POCl$_3$ or functionalized Vilsmeier reagents can be applied to other porphyrinic compounds containing sulfonic acid groups, such that the corresponding sulfonylchloride compounds can be formed. An exemplary (partial) list of such compounds is presented in Table 1.

Table 1

Figure 2:
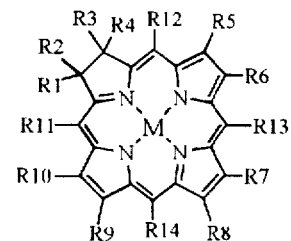
Figure 3:
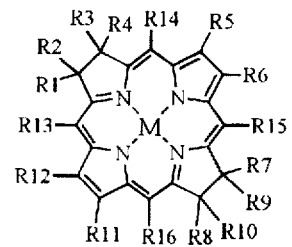
Figure 4:
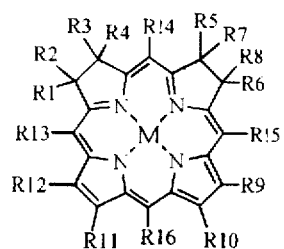
Figure 5:
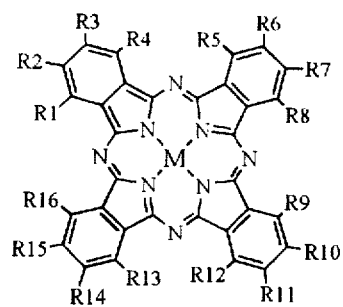
Figure 6:
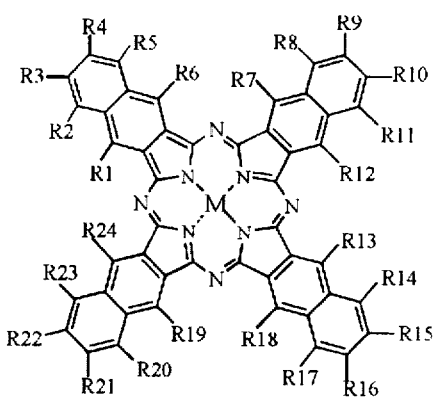
Figure 7:
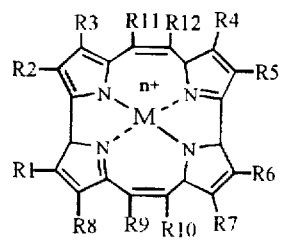
Figure 8:
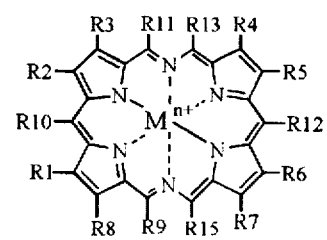
Figure 9:
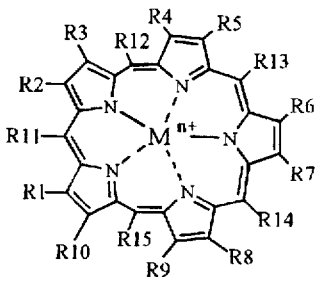
Figure 10:
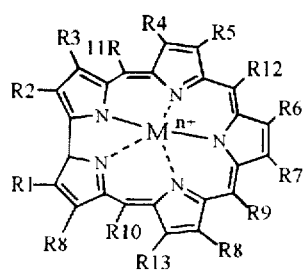
Figure 11:
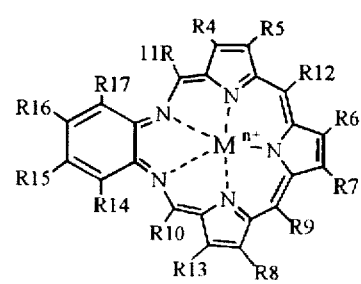
Figure 12:
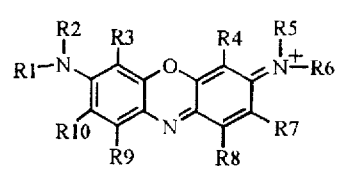
Figure 13:
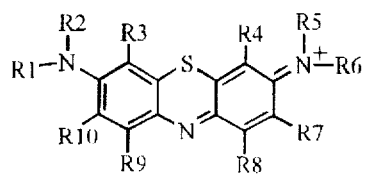
Figure 14:
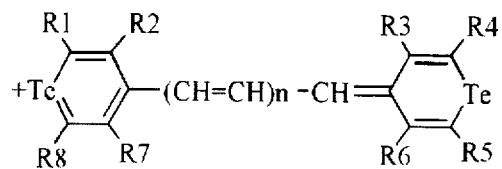
Figure 15:
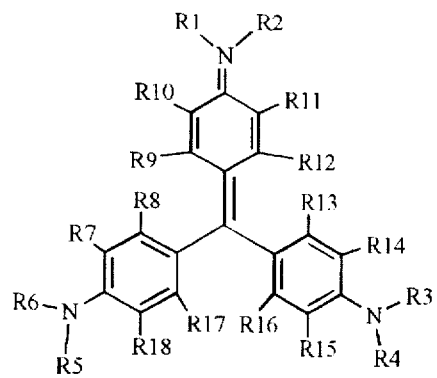
Figure 16:
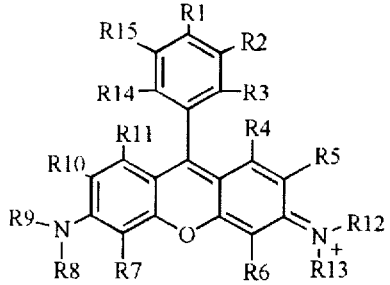
Figure 17:
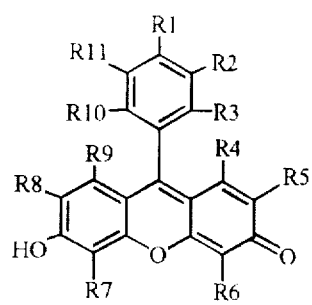
Figure 18:
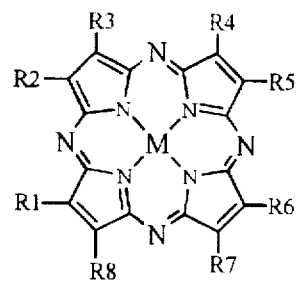
Figure 19:
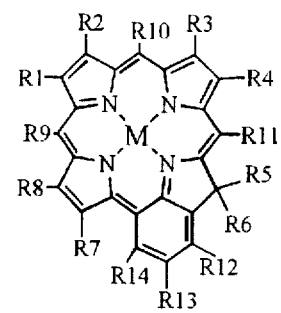
Figure 20:
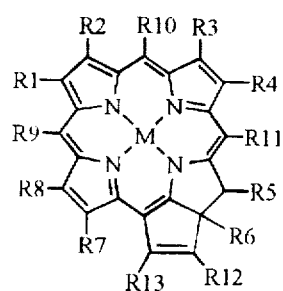
Figure 21:
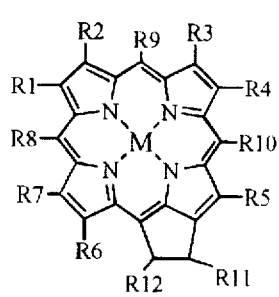
Figure 22:
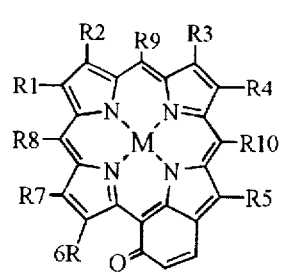

Pyrrole-derived macrocyclic compounds
Naturally occurring or synthetic porphyrins and derivatives thereof (FIG. 1)
Naturally occurring or synthetic chlorins and derivatives thereof (FIG. 2)
Naturally occurring or synthetic bacteriochlorins and derivatives thereof (FIG. 3)
Synthetic isobacteriochlorins and derivatives thereof (FIG. 4)
Phthalocyanines and derivatives thereof (FIG. 5)
Naphthalocyanines and derivatives thereof (FIG. 6)
Porphycenes and derivatives thereof (FIG. 7)
Porphycyanines and derivatives thereof (FIG. 8)
Pentaphyrin and derivatives thereof (FIG. 9)
Sapphyrins and derivatives thereof (FIG. 10)
Texaphyrins and derivatives thereof (FIG. 11)
Phenoxazine dyes and derivatives thereof (FIG. 12)
Phenothiazines and derivatives thereof (FIG. 13)
Chaloorganapyrylium dyes and derivatives thereof (FIG. 14)
Triarylmethanes and derivatives thereof (FIG. 15)
Rhodamines and derivatives thereof (FIG. 16)
Fluorescenes and derivatives thereof (FIG. 17)
Azaporphyrins and derivatives thereof (FIG. 18)
Benzochlorins and derivatives thereof (FIG. 19)
Purpurins and derivatives thereof (FIG. 20)
Chlorophylls and derivatives thereof (FIG. 21)
Verdins and derivatives thereof (FIG. 22)

The following examples are intended to illustrate the application of the method for functionalizing macrocycles in accordance with the present invention. The following examples are exemplary and are not to be construed as limiting the scope of the invention.

EXAMPLE 1

Octaethylbenzochlorin sulfonyl chloride (OEBCSC)

(phosphorus oxychloride method)

Octaethylbenzochlorin sulfonic acid (0.4 g) is dissolved in phosphorus oxychloride (5 mL) and the solution refluxed for 2 hrs. The phosphorus oxychloride was removed by rotary evaporation and the solid dissolved in dichloromethane (5 mL). Triethylamine (0.5 mL) was added dropwise with stirring to neutralize the solution. The solution was immediately columned on silica using 20% hexane/dichloromethane and the major brown fraction collected and precipitated from dichloromethane hexane. The solid was collected by filtration and dried to give 365 mg of OEBCSC.

Octaethylbenzochlorin sulfonyl chloride (OEBCSC)

(Vilsmeier reagent method)

Phosphorus oxychloride (0.5 mL) was added dropwise to ice cold dimethylformamide (0.5 mL) with swirling. The solution was left to warm to room temperature for 20 minutes. Octaethylbenzochlorin sulfonic acid (0.4 g) was dissolved in dichloromethane (10 mL) and the Vilsmeier reagent (1 mL) prepared previously was added to the solution. After stirring at room temperature for 15 minutes, the solution was poured cautiously into ice cold water (100 mL) and the organic layer washed and rapidly separated. The organic layer was dried over sodium sulfate, filtered and reduced in volume to ~5 mL by rotary evaporation. Triethylamine (0.5 mL) was added and the resulting solution was immediately columned on silica using 20% hexane/dichloromethane and the major brown fraction collected and precipitated from dichloromethane/hexane. The solid was collected by filtration and dried to give 375 mg of OEBCSC.

EXAMPLE 2

Octaethylbenzochlorin sulfonyihexylamide

To a stirred solution of octaethylbenzochlorin sulfonylchloride (300 mg) in dry dichloromethane (5 mL), was added hexylamine (200 mg) in dry dichloromethane (20 ml). The resulting solution was stirred at room temperature for 30 min and triethylamine 0.1 mL was added. After stirring at room temperature for an additional 10 min, the solvent was removed by rotary evaporation. The crude residue was columned on silica using dichloromethane and the major grey band collected and recrystallized from dichloromethane/methanol to give the title compound.

EXAMPLE 3

Zinc octaethylbenzochlorin sulfonyl(ethoxyethanol)amide. (ZnOEBCSA(ethoxyethanol))

To a stirred solution of octaethylbenzochlorin sulfonylchloride (300 mg) in dichloromethane (50 mL), was added 2-(2-aminoethoxy)ethanol (150 mg) in dichloromethane (20 ml) and dry triethylamine (0.1 mL). The resulting solution was stirred at room temperature for 1 hr. Zinc acetate (200 mg) dissolved in methanol (15 mL) was added to the reaction solution and the solution was warmed on a hot water bath until metallation of the benzochlorin was complete by Uv/vis spectroscopy (as seen by a band I absorption at 675 nm). The solvent was then removed by rotary evaporation and the crude residue redissolved in dichloromethane (5 mL) and chromatographed on silica using dichloromethane. The major green band collected and recrystallized from dichloromethane/methanol to give the title compound.

EXAMPLE 4

Copper Octaethylbenzochlorin hexylsulphonylamide iminium salt. (CuiminOEBCSHA)

To copper octaethylbenzochlorin sulfonic acid (300 mg) dissolved in dichloromethane (100 mL) was added (chloromethylene)dimethylammonium chloride (500 mg) and the solution stirred overnight at room temperature. The solution was poured into ice cold water and the organic layer washed and separated rapidly and dried over sodium sulfate. The solution was filtered to remove the sodium sulfate and hexylamine (100 mg) in dichloromethane (2 mL) was added. The solution was stirred for 20 minutes at room temperature, then poured into water. The organic layer was washed with dilute HCl and dried over sodium sulfate. The solution was filtered and evaporated to dryness. The remaining reside was chromatographed on silica using 2% methanol/dichloromethane and the major green band collected and evaporated. The title compound was obtained as a green powder by precipitation from dichloromethane/hexane.

EXAMPLE 5

5,10,15,29-Tetraphenyl-21H,23H-porphine-p,p',p",p'''-tetrasulfonylhexylamide.(TPPSHA)

5,10,15,29-Tetraphenyl-21H,23H-porphine-p,p',p", p'''-tetrasulfonic acid (200 mg) was added to methylene chloride (100 mL) and (chloromethylene)dimethylammonium chloride (500 mg) was added. After 1 hr stirring at room temperature, the solution was poured into ice cold water and the organic layer washed and separated rapidly and dried over sodium sulfate. The solution was filtered to remove the sodium sulfate and hexylamine (1 mL) in dichloromethane (2 mL) was added. The solution was stirred for 20 minutes at room temperature, then poured into water. The organic layer was washed with dilute HCl and water and dried over sodium sulfate. The solution was filtered and evaporated to dryness. The remaining reside was chromatographed on silica using 2% methanol/dichloromethane and the major red band collected and evaporated. The title compound was obtained as a red powder by precipitation from dichloromethane/methanol.

EXAMPLE 6

Deuteroporphyrin IX 2,4 disulfonylhexylamide. (DPDSHA)

Deuteroporphyrin-IX 2,4-disulfonic acid (100 mg) is dissolved in dichloromethane (100 mL) and (chloromethylene) dimethylammonium chloride (500 mg) was added. The solution stirred for 3 hrs at room temperature. The solution was then poured into ice cold water and the organic layer washed and separated rapidly and dried over sodium sulfate. The solution was filtered to remove the sodium sulfate and hexylamine (100 mg) in dichloromethane (2 mL) was added. Dry triethylamine (0.1 mL) was added and the solution was stirred for 20 minutes at room temperature, then poured into water. The organic layer was washed with dilute HCl, followed by dilute sodium bicarbonate solution and water and dried over sodium sulfate. The solution was filtered and evaporated to dryness. The remaining reside was chromatographed on silica using 2% methanol/dichloromethane and the major red band collected and evaporated. The title compound was obtained as a red powder by precipitation from dichloromethane/hexane.

Meso-Halogenation Reactions using Thionyl chloride

EXAMPLE 7

5,15-dichlorooctaethylbenzochlorin. (DCOEBC)

Octaethylbenzochlorin (100 mg) was dissolved in thionylchloride (5 mL) and the solution refluxed for 1.5 hrs. The solvent was removed and the residue dissolved in dichloromethane (3 mL) and neutralized with triethylamine (0.2 mL). The solution was chromatographed on silica using dichloromethane as eluent. The major green fraction was collected and recrystallized from dichloromethane/methanol.

EXAMPLE 8 meso-Chlorinated etioporphyrin I (CEtI) and 5,15-dichlorinated etioporphyrin I (DCEtI)

Etioporphyrin I (69 mg) was dissolved in thionylchloride (5mL) and the solution refluxed for approximately 1.5 hrs until all the starting material had been consumed as observed by thin layer chromatography. The excess thionylchloride was removed by rotary evaporation and residue was dissolved in dichloromethane and washed with aqueous sodium bicarbonate solution and water. The organic layer was collected and evaporated by rotary evaporator. The residue was columned on silica using dichloromethane/hexane (1:1). Two major fractions were collected, the first contained the 5,15-dichlorinated etioporphyrin I while the second contained the mono-chlorinated etioporphyrin I.

Other Applications

The novel derivatives of known compounds prepared by the method described herein may be useful for NMR imaging of diseased target tissue in an organism. For example porphyrins or pyrrolic compounds or indeed many other organic compounds containing magnetic resonance imaging. The suitability of these compounds as MRI agents is largely dependent on the selective localization of these compounds at the disease site. Hence compounds containing these and other MRI active metals that have been prepared via the chemistry outlined above, may be useful tools as MRI agents.

Compounds having the form $ASO_2B$ wherein either A or B contain a radioactive isotope such as $^{14}C$, $^{3}H$, $^{131}I$ and others, may have application in diagnosis of diseased target tissue. The chemistry outlined above lends itself well to the attachment of radioactive derivatives of A to compound B or radioactive derivatives of B to A.

The synthesis of compounds linked to nucleoside bases is an area of growing importance. Such compounds are currently being tested for tumoricidal activity against human malignant melanoma, as antiviral agent in blood purification including HIV-1 and as novel synthetic DNA intercelating agents. The synthesis-of compounds of the structure $ASO2B$, where either A or B is a nucleoside or a polynucleoside is greatly facilitated by the chemistry outlined above.

These examples are particularly pertinent to the functionalization of $R_n$-substituted macrocyclic compounds wherein one or more of the $R_n$ groups contain a sulfonic acid moiety capable of being modified through the use of $POCl_3$ or a suitable Vilsmeier reagent to form a sulfonylchloride moiety or an iminium group. While pertinent embodiments of the present invention have been illustrated and described, it would be obvious to those skilled in the art that various other changes and modifications can be made without departing from the spirit and scope of the invention. For example, photosensitive reaction products made in accordance with the present teaching may be either linked to other compounds such as nucleotides, nucleosides, and antibodies or used alone to locate and/or diagnose a diseased tissue. In addition, such compounds of the form $ASO_2B$ are useful for the phototherapy of a variety of disease conditions such as vascular, cardiovascular or ebrovascular disease; viral-induced conditions, precancerous conditions, glaucoma, endometriocis and even dysfunctional uterine bleeding. It is, therefore, intended to cover in the appended claims all such changes and modifications in the method or in reaction products derived therefrom that are within the scope of this invention.

What I claim is:

1. A composition of matter comprising a photosensitive compound having the formula $ASO_2R$ wherein A comprises a benzochlorin compound having a sulfonyl group attached thereto and wherein R is a compound containing a reactive carboxyl or amine group.

2. A composition of matter comprising a compound having the formula $ASO_2NHR$ wherein A is benzochlorin having a sulfonyl group attached thereto and wherein R is a compound containing a reactive carboxyl or amine group.

3. A composition of matter comprising a compound having the general formula $ASO_2X$, wherein A is a substituted tetrapyrrole having the following structure:

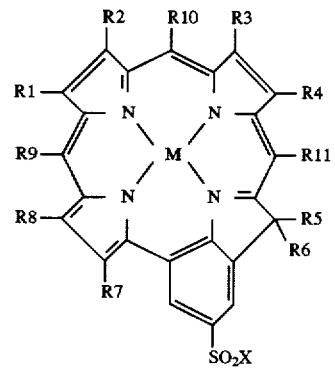

wherein

R1–R8 are selected from the group consisting of alkyl, aryl, substituted aryl, alkenyl, substituted alkenyl, alkyne, CHO, CH$_2$OH, CH$_2$O-alkoxy and (CH$_2$)$_n$CO$_2$R13, wherein R13 is selected from the group consisting of H, alkyl or aryl and n=1,2,3;

R9–R11 are selected from the group consisting of H, halogens, alkyl, aryl, substituted aryl, alkenyl, substituted alkenyl, alkyne, CHO, CH$_2$OH, CH$_2$O-alkoxy, CH=N(R13,R14)$^+$ X$^-$ (where R13 and R14 are either alkyl, aryl or cyclic alkyl), (CH$_2$)$_n$CO$_2$R13 (where n is 2 or 3), R13 is H, alkyl or aryl or a pharmaceutically acceptable salt;

X is a halide; or a compound having a reactive carboxyl or amino group thereon and having a molecular weight less than or equal to 2000 daltons; and M is either 2H or a metal selected from the group consisting of: Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, Ti, Tm, U, V, Y, By, Zn, and Zr and radioactive isotopes thereof.

4. A composition of matter having the general formula A(SO$_2$R6)$_2$, wherein A is a substituted tetrapyrrole having the following structure:

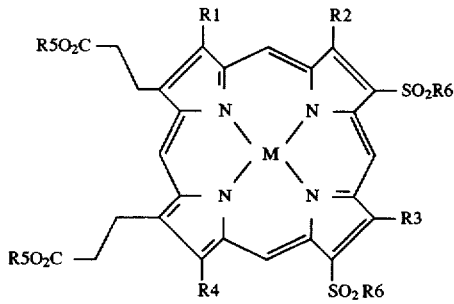

wherein

R1–R4 are CH$_3$ or alkyl, aryl, substituted aryl, alkenyl, substituted alkenyl, alkyne, CHO, CH$_2$OH or CH$_2$O-alkoxy, (CH$_2$)$_n$CO$_2$R13, where R13 is H, alkyl or aryl;

R5 are H, alkyl, aryl, substituted aryl, a pharmaceutically acceptable salt, (CH$_2$)$_n$O-alkoxy, where n is 1 or 2;

R6 are halides or groups less than or equal to 2000 daltons;

M is either 2H or a metal selected from the group consisting of Ag, Al, Ce, Co, Cr, Cu, Dy, Er, Eu, Fe, Ga, Gd, Hf, Ho, In, La, Lu, Mn, Mo, Nd, Pb, Pd, Pr, Pt, Rh, Sb, Sc, Sm, Sn, Tb, Tl, Tm, U, V, Y, By, Zn, and Zr and isotopes thereof.

5. Compounds in accordance with the composition of matter of claim 1 or claim 4 wherein the compound is enriched with radioactive atoms.

6. A method for diagnosing a disease in an organism which comprises the following steps:

(a) administering a compound in accordance with the composition of matter of claim 2 to an organism;

(b) waiting a period of time sufficient for the compound to accumulate in a target tissue within the organism until a ratio comprising the concentration of the compound in the diseased tissue divided by the concentration of the compound in surrounding healthy tissue is maximized;

(c) detecting and measuring the ratio in accordance with step (b) in the target tissue by an instrument operable for detecting ionizing radiation.

7. A compound in accordance with the composition of matter of claim 3 or claim 2 wherein the compound is linked to at least one antibody.

\* \* \* \* \*